(12) United States Patent
Bischoff et al.

(10) Patent No.: US 8,337,877 B2
(45) Date of Patent: *Dec. 25, 2012

(54) REDUCTION OF INFECTION ASSOCIATED WITH MEDICAL DEVICE

(75) Inventors: Thomas C. Bischoff, Minneapolis, MN (US); William V. Ferris, Jr., Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/083,983

(22) Filed: Apr. 11, 2011

(65) Prior Publication Data

US 2011/0189256 A1 Aug. 4, 2011

Related U.S. Application Data

(63) Continuation of application No. 12/104,932, filed on Apr. 17, 2008, now Pat. No. 7,947,301.

(60) Provisional application No. 60/912,234, filed on Apr. 17, 2007.

(51) Int. Cl.
*A61K 9/00* (2006.01)
*A61K 31/496* (2006.01)
*A61P 31/00* (2006.01)

(52) U.S. Cl. ............... 424/423; 514/254.11; 424/400

(58) Field of Classification Search .................. None
See application file for complete search history.

(56) References Cited

U.S. PATENT DOCUMENTS

| | | | | |
|---|---|---|---|---|
| 5,217,493 A * | 6/1993 | Raad et al. | .............. | 623/11.11 |
| H001465 H | 7/1995 | Stokes | | |
| 5,820,607 A | 10/1998 | Tcholakian | | |
| 5,902,283 A | 5/1999 | Darouiche | | |
| 6,162,487 A | 12/2000 | Darouiche | | |
| 6,451,003 B1 | 9/2002 | Prosl | | |
| 6,528,107 B2 * | 3/2003 | Chinn et al. | ............. | 427/2.24 |
| 6,843,784 B2 | 1/2005 | Modak | | |
| 6,884,741 B2 * | 4/2005 | Batdorf | ............. | 442/123 |
| 6,887,270 B2 | 5/2005 | Miller | | |
| 6,968,234 B2 | 11/2005 | Stokes | | |
| 7,596,408 B2 | 9/2009 | Singhal | | |
| 2004/0186528 A1 | 9/2004 | Ries | | |
| 2005/0079199 A1 | 4/2005 | Heruth | | |
| 2005/0267543 A1 | 12/2005 | Heruth | | |
| 2006/0009806 A1 | 1/2006 | Heruth | | |
| 2006/0039946 A1 * | 2/2006 | Heruth et al. | ............. | 424/422 |
| 2006/0051392 A1 | 3/2006 | Heruth | | |
| 2008/0125728 A1 | 5/2008 | Bischoff | | |

FOREIGN PATENT DOCUMENTS

| | | |
|---|---|---|
| EP | 640661 | 3/1995 |
| WO | WO 96/039215 | 12/1996 |
| WO | WO 2004/084955 | 10/2004 |
| WO | WO 2005/058414 | 6/2005 |
| WO | WO 2005/058414 * | 6/2006 |

OTHER PUBLICATIONS

PCT Search Report and Written Opinion dated May 28, 2009.

\* cited by examiner

*Primary Examiner* — Robert A Wax
*Assistant Examiner* — Danah Al-Awadi

(57) ABSTRACT

Anti-infective articles capable of preventing infection associated with implantation of medical devices include low levels of anti-infective agents, may cover only a fraction of the portion of the medical device and be effective, or may rapidly elute anti-infective agent, without sustained elution, and still be effective.

15 Claims, 6 Drawing Sheets

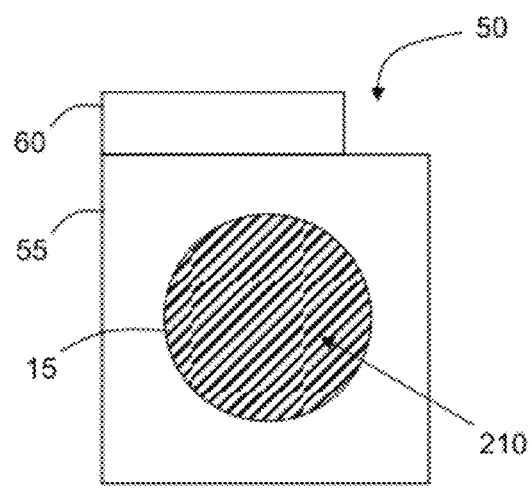
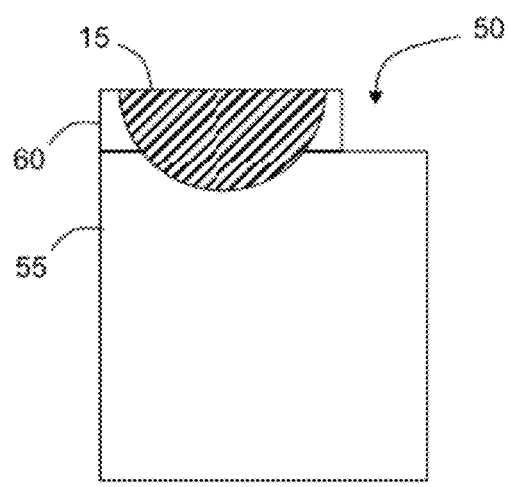
FIG. 4A    FIG. 4B
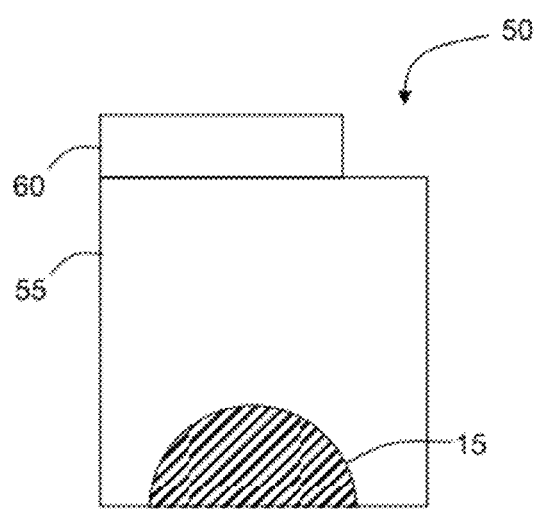
FIG. 4C

| Cover Design: | Thin Boot (2 Holes) | Thick Boot (2 Holes) | Thick Boot | Thin Disc | Thick Disc |
|---|---|---|---|---|---|
| Drawing: | | | | | |
| Polymer: | Silicone (LSR) Dow Corning 4850 (0.005") | Silicone (LSR) Dow Corning 4850 (0.015") | Silicone (HTV) Dow Corning 4735 (0.015") | Silicone (LSR) Dow Corning 4850 (0.005") | Silicone (LSR) Dow Corning 4850 (0.015") |
| Drug Content | | | | | |
| Minocycline Rifampin | 778-865 µg 832-998 µg | 593 µg 973 µg | 13124 µg 19552 µg | 163-190 µg 192-203 µg | 929 µg 1040 µg |
| Ratio: Minocycline: Rifampin | 1:1.1 | 1:1.2 | 1:1.47 | 1:1.1 | 1:1.12 |
| 7 Day In-Vivo Elution | | | | | |
| Minocycline Rifampin | 778-865 µg 832-998 µg | 4782 µg 2810 µg | 16611 µg 6911 µg | 168-190 µg 195-203 µg | 873 µg 574 µg |
| Colonized Devices in Animal (Rabbit) Efficacy Studies | | | | | |
| Study # | w/o Extensions (Controls) | w/ Extensions (Controls) | w/o Extensions (Controls) | w/ Extensions (Controls) | w/o Extensions (Controls) |
| 53464 [n=20] | | 0/5 | | 0/5 (5/5) | |
| 53482 [n=25] | 0/7 (7/7) | | | | 1/7 (7/7) |
| 5082 3 [n=10] | | | 0/10 (7/8) | | |
| 4821 4 [n=10] | | | 0/10 (8/8) | 0/7 (7/7) | |

FIG. 9

REDUCTION OF INFECTION ASSOCIATED WITH MEDICAL DEVICE

RELATED APPLICATION

This application is a continuation application of Ser. No. 12/104,932 filed Apr. 17, 2008 which claims the benefit of Provisional Application No. 60/912,234, filed on Apr. 17, 2008, which applications are hereby incorporated herein by reference in their entirety.

FIELD

This disclosure relates, inter alia, to implantable medical devices. More particularly, it relates to systems, devices and methods for preventing infection associated with implantation of implantable medical devices.

BACKGROUND

A wide variety of implantable medical devices (IMDs) are commercially available for clinical implantation, including cardiac pacemakers, cardioverter/defibrillators having pacing capabilities, other electrical stimulators including spinal cord, deep brain, nerve, and muscle stimulators, drug delivery systems, cardiac and other physiologic monitors, cochlear implants, etc. Such IMDs often contain a battery powered component that is implanted subcutaneously at a surgically prepared site, referred to as a "pocket". Associated devices, such as medical leads and catheters, extend from the subcutaneous site to other subcutaneous sites or deeper into the body to organs or other implantation sites.

The surgical preparation and initial or replacement IMD implantations are conducted in a sterile field, and the IMD components are packaged in sterile containers or sterilized prior to introduction into the sterile field. However, despite these precautions, there always is a risk of introduction of microbes into the pocket. Surgeons therefore typically apply disinfectant or antiseptic agents to the skin at the surgical site prior to surgery, directly to the site before the incision is closed, and prescribe oral antibiotics for the patient to ingest during recovery.

Despite these precautions, infections do occur. In addition, once the pocket becomes infected, the infection can migrate along the lead or catheter to the heart, brain, spinal canal or other location in which the lead or catheter is implanted. Such a migrating infection can become intractable and life-threatening, requiring removal of the IMD in the pocket and associated devices, such as leads and catheters. Removal of a chronically implanted lead or catheter can be difficult and dangerous. Aggressive systemic drug treatment is also provided to treat the infection.

Impregnating, coating or otherwise disposing one or more anti-infective agent in, on or about an IMD has been proposed. Some such IMDs are currently commercially available. However, the use of anti-infective agents with permanently or temporarily implantable IMDs raises concerns such as development of strains of microbes resistant to the anti-infective agents and the development of allergic reactions to the anti-infective agents associated with the IMD. The presence of low levels of anti-infective agents over time raises concerns regarding the development of resistant strains of microbes, and large amounts or the presence of anti-infective agent over time raises concerns regarding development of an allergic reaction.

SUMMARY

The present disclosure describes, inter alia, systems, devices and methods that can be used to prevent infection associated with implantation of medical devices. The use of low levels of anti-infective agents has been shown to be effective in preventing such infection. In addition, it has been shown that anti-infective agents that are not placed over a large portion of an implantable medical device are still effective at preventing infection around the entire device following implantation. Further, it has been unexpectedly shown that rapid elution of anti-infective agent from a polymeric matrix, without sustained elution, is sufficient to prevent infection. Systems and methods that employ low levels of anti-infective agents or rapidly eluting anti-infective articles should reduce the likelihood of development of resistant strains of microbes and development of an allergic reaction.

In various embodiments, the invention provides an implantable medical system. The system includes an implantable medical device having (i) an exterior surface having a surface area, and (ii) an article configured to contact the exterior surface. The article includes minocycline in an amount of between 1 and 500 micrograms per square inch of the exterior surface area of the device and rifampin in an amount between 1 and 500 micrograms per square inch of the exterior surface area of the device. In various embodiments, minocycline is present in the article in an amount between 1 and 100 micrograms (e.g., between 3 and 50 micrograms or between 5 and 25 micrograms) per square inch of the exterior surface area of the device and wherein rifampin is present in the article in an amount between 1 and 100 micrograms (e.g., between 3 and 50 micrograms or between 5 and 25 micrograms) per square inch of the exterior surface area of the device. In various embodiments, the article includes a polymeric material, such as silicone, and may be formed substantially from a polymeric material. In various embodiments, the article has an average thickness of 0.01 inches or less (e.g., 0.0075 inches or less or 0.005 inches or less). In various embodiments, the article has first and second major surfaces, with the first major surface being in contact with the device and the second major surface having a surface area of 30% or less than the exterior surface area of the device.

In various embodiments, the invention provides an implantable medical system. The system includes an implantable medical device having (i) an exterior surface having a surface area, and (ii) an article configured to contact the exterior surface. The article has an average thickness 0.01 inches or less and contains an effective amount of one or more anti-infective agents, such as minocycline and rifampin. In various embodiments, the article has an average thickness of 0.0075 inches or less or 0.005 inches or less. In various embodiments, minocycline is present in the article in an amount of between 1 and 1500 micrograms (e.g., between 3 and 750 micrograms or between 5 and 400 micrograms) per square inch of the exterior surface area of the device, and rifampin is present in the device in an amount of between 1 and 1500 micrograms (e.g., between 3 and 750 micrograms or between 5 and 400 micrograms) per square inch of the exterior surface area of the device.

In various embodiments, the invention provides an implantable medical system. The system includes an implantable medical device having (i) an exterior surface having a surface area, and (ii) an article configured to contact with the exterior surface area. The article has first and second major surfaces. The second major surface has a surface area of 30% or less (e.g., 20% or less, 10% or less, or 5% or less) than the exterior surface area of the device. The article contains an effective amount of one or more anti-infective agents, such as minocycline and rifampin.

In various embodiments, the invention provides an implantable medical system. The system includes (i) an implantable medical device having an exterior surface having a surface area, and (ii) an article configured to contact the exterior surface. The article contains an anti-infective agent in an amount per square inch of the exterior surface area of the device. The amount of the anti-infective agent is: (the minimum inhibitor concentration against a strain of S. aureus in an amount per milliliter) times (one milliliter) times (a number between the range of 1,500 and 50,000).

In various embodiments, the invention provides an implantable medical system. The system includes an implantable medical device having (i) an exterior surface having a surface area, and (ii) an article configure to contact the exterior surface. The article includes an effective amount of one or more anti-infective agents, such as minocycline and rifampin. The article is configured to elute 40% or more of the anti-infective agents within 48 hours of being implanted in a patient. In various embodiments, the article is configured to elute 60% or more of the anti-infective agent within 24 hours of being implanted in a patient. In various embodiments, the article is configured to release substantially all the anti-infective agent with 24 hours. In various embodiments, the article is configured to release substantially all the anti-infective agent with 72 hours. In various embodiments, the anti-infective agent includes minocycline and the article is configured to release substantially all the minocycline within 24 hours of being implanted. In various embodiments, the anti-infective agent includes rifampin and the article is configured to release substantially all the rifampin within 72 hours of being implanted.

In various embodiments, the invention provides an implantable medical system. The system includes an implantable medical device having (i) an exterior surface having a surface area, and (ii) an article configured to contact the exterior surface area. The article includes (i) minocycline in an amount of between 100 and 2000 and (ii) rifampin in an amount between 1000 and 2000 micrograms. In various embodiments, the article has an average thickness of 0.01 inches or less (e.g., 0.0075 inches or less or 0.005 inches or less).

In various embodiments, the invention provides a method for preventing infection in proximity to an implanted medical device. The method includes implanting, in proximity to the implanted device, an article containing an anti-infective agent in a patient. The article has first and second opposing major surfaces. The surface area of the second surface of the article is 30% or less than an exterior surface area of the implantable medical device. The method further includes eluting the anti-infective agent from the article to prevent an infection from forming in proximity to the implanted device. In various embodiments, implanting the article includes implanting the device, with which the article is in contact. In various embodiments, eluting the anti-infective agent from the article includes eluting 60% or more of the anti-infective agent within 24 hours of implanting the article.

In various embodiments, the invention provides a method for preventing infection in proximity to an implanted medical device. The method includes implanting, in proximity to the implanted device, an article containing an anti-infective agent in a patient. The article has an average thickness 0.01 inches or less. The method further includes eluting the anti-infective agent from the article to prevent an infection from developing in proximity to the implanted device. In various embodiments, implanting the article includes implanting the device, with which the article is in contact. In various embodiments, eluting the anti-infective agent from the article includes eluting 60% or more of the anti-infective agent within 24 hours of implanting the article.

In various embodiments, the invention provides a method for preventing infection in proximity to an implanted medical device. The method includes implanting, in proximity to the implanted device, an article containing an anti-infective agent in an amount per square inch of the exterior surface area of the device. The amount of the anti-infective agent is: (the minimum inhibitor concentration against a strain of S. aureus in an amount per milliliter) times (one milliliter) times (a number between the range of 1,500 and 50,000). The method further includes eluting the anti-infective agent from the article to prevent an infection from forming in proximity to the implanted device. In various embodiments, implanting the article includes implanting the device, with which the article is in contact. In various embodiments, eluting the anti-infective agent from the article includes eluting 60% or more of the anti-infective agent within 24 hours of implanting the article.

In various embodiments, the invention provides a method for preventing infection in proximity to an implanted medical device. The method includes implanting, in proximity to the implanted device, an article comprising (i) minocycline in an amount of between 1 and 500 micrograms per square inch of the exterior surface area of the device and (ii) rifampin in an amount between 1 and 500 micrograms per square inch of the exterior surface area of the device. The method further includes eluting the anti-infective agent from the article to prevent an infection from forming in proximity to the implanted device. In various embodiments, implanting the article includes implanting the device, with which the article is in contact. In various embodiments, eluting the anti-infective agent from the article includes eluting 60% or more of the anti-infective agent within 24 hours of implanting the article.

In various embodiments, the invention provides a method for preventing infection in proximity to an implanted medical device. The method includes implanting, in proximity to the implanted device, an anti-infective article having (i) minocycline in an amount of between 100 and 2000 and (ii) rifampin in an amount between 100 and 2000 micrograms. The method further includes eluting the minocycline and rifampin from the article to prevent an infection from forming in proximity to the implanted device. In various embodiments, implanting the article includes implanting the device, with which the article is in contact. In various embodiments, eluting the anti-infective agent from the article includes eluting 60% or more of the anti-infective agent within 24 hours of implanting the article.

In various embodiments, the invention provides a method for preventing infection in proximity to an implanted medical device. The method includes implanting, in proximity to the implanted device, an anti-infective article containing effective amounts of minocycline and rifampin. The method further includes eluting the minocycline and rifampin from the article to prevent an infection from forming in proximity to the implanted device such that at five days following implantation 300 micrograms or less of the minocycline or rifampin remain in the article.

In various embodiments, the invention provides kits containing the components of the systems or methods described above or the articles in the systems or methods described above.

By providing devices, systems and methods that incorporate lower levels of anti-infective agents or that rapidly elute anti-infective agents concerns associated with development of antibiotic resistance or and allergic reaction can be minimized. These and other advantages will be readily understood from the following detailed descriptions when read in conjunction with the accompanying drawings.

BRIEF DESCRIPTION OF THE DRAWINGS

FIG. 4A-C are diagrammatic representations of side views of representative anti-infective articles associated with a representative implantable device.

FIG. 9 is a summary of results testing the efficacy, drug content and drug elution of various anti-infective articles.

The drawings are not necessarily to scale. Like numbers used in the figures refer to like components, steps and the like. However, it will be understood that the use of a number to refer to a component in a given figure is not intended to limit the component in another figure labeled with the same number.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used herein, an "effective amount" of an anti-infective agent is an amount that prevents, reduces the severity of, or delays an infection.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Unless otherwise indicated, all numbers expressing feature sizes, amounts, and physical properties used in the specification and claims are to be understood as being modified in all instances by the term "about" Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

The present disclosure describes, inter alia, systems, devices and methods that can be used to prevent infection associated with implantation of medical devices. In various embodiments, methods, systems and devices that use of low levels of anti-infective agents, that rapidly elute anti-infective agent, e.g. from a polymeric matrix, or that employ anti-infective articles that cover only a portion of, or are only a fraction of the surface area of, an implantable device are described.

Figure 1:
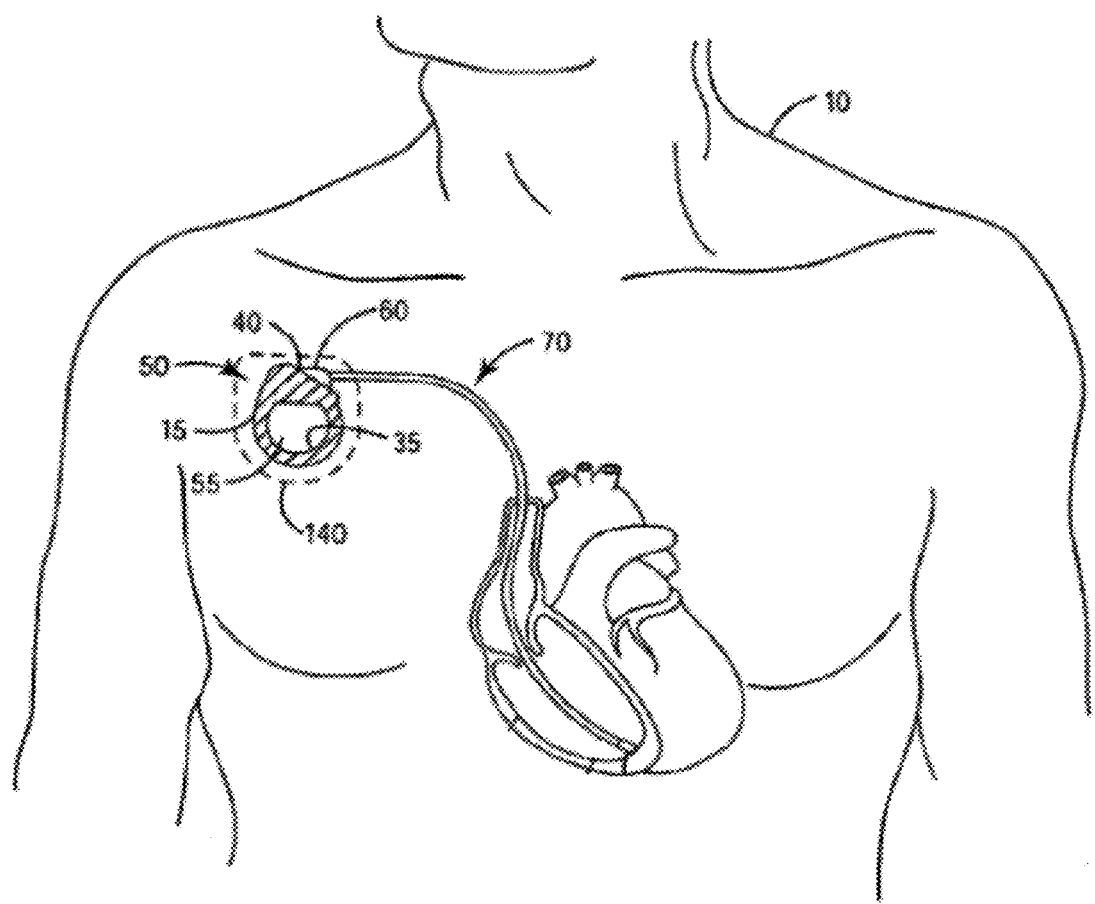
FIG. 1 is a diagrammatic representation of a representative environment of a system implanted in a patient.

Referring to FIG. 1, a general environment of an implantable device 50 implanted in a patient is shown. In the embodiment depicted in FIG. 1, device 50 is a ventricular pacemaker, but it will be understood that the teachings of provided herein may be applied with regard to any implantable medical device, such as a defibrillator, an infusion device, a neurostimulator, a monitoring device, a cochlear implant, a medical lead, a medical catheter, or the like. As shown in FIG. 1, device 50 is implanted in a subcutaneous pocket 140 of a patient 10. Device 50 as shown is implanted pectorally, but it will be understood that device may be implanted at any medically acceptable location of patient 10, including in the abdomen. An anti-infective article 15 is shown as being disposed about device 50, but may be disposed on or generally located in proximity to device 50. Article 15 as depicted includes a side opening 35, exposing a portion of housing 55 of device 50. Article 15 as depicted also includes an edge opening 40 allowing for a connector block 60 of device 50 to be exposed to facilitate connection of an associated device 70 to device 50. Associated device 70 shown in the embodiment depicted in FIG. 1 is a lead, but may be any suitable device such as a lead or catheter, as appropriate.

In general, any suitable anti-infective agent may be used in association with an anti-infective article. For example, one or more antibiotic suitable for use in a human may be employed in accordance with various embodiments presented herein. The antibacterial agent may have bacteriostatic or bacteriocidal activities. Nonlimiting examples of classes of antibiotics that may be used include tetracyclines (e.g. minocycline), rifamycins (e.g. rifampin), macrolides (e.g. erythromycin), penicillins (e.g. nafcillin), cephalosporins (e.g. cefazolin), other beta-lactam antibiotics (e.g. imipenem, aztreonam), aminoglycosides (e.g. gentamicin), chloramphenicol, sulfonamides (e.g. sulfamethoxazole), glycopeptides (e.g. vancomycin), quinolones (e.g. ciprofloxacin), fusidic acid, trimethoprim, metronidazole, clindamycin, mupirocin, polyenes (e.g. amphotericin B), azoles (e.g. fluconazole) and beta-lactam inhibitors (e.g. sulbactam). Nonlimiting examples of specific antibiotics that may be used include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin. One of ordinary skill in the art will recognize that other antibiotics may readily be used.

It is desirable that the antibiotic(s) selected kill or inhibit the growth of one or more bacteria that are associated with infection following surgical implantation of a medical device. Such bacteria are recognized by those of ordinary skill in the art and include *Staphylococcus aureus* and *Staphylococcus*

*epidermis*. To enhance the likelihood that bacteria will be killed or inhibited, it may be desirable to combine one or more antibiotic. It will be recognized by one of ordinary skill in the art that antimicrobial agents having different mechanisms of action or different spectrums of action may be most effective in achieving such an effect. In particular embodiments, rifampin and micocycline are used in combination.

Referring to FIG. 2, diagrammatic illustrations of side views of representative anti-infective articles 15 are shown. Article 15 may be any suitable shape and may take any suitable form. For example, article 15 may be in the form of a tube, sheath, sleeve, boot, disc, or the like. Article 15 may be formed from polymeric material and may be extruded, molded, or otherwise formed. Examples of commonly used suitable polymeric materials include organic polymers such as silicones, polyamines, polystyrene, polyurethane, acrylates, polysilanes, polysulfone, methoxysilanes, and the like. Other polymers that may be utilized include polyolefins, polyisobutylene and ethylene-alphaolefin copolymers; acrylic polymers and copolymers, ethylene-covinylacetate, polybutylmethacrylate; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; carboxymethyl cellulose; polyphenyleneoxide; and polytetrafluoroethylene (PTFE).

Article 15 may comprise a biodegradable polymeric material, such as synthetic or natural bioabsorbable polymers. Synthetic bioabsorbable polymeric materials that can be used to form the coating layers include poly(L-lactic acid), poly-caprolactone, poly(lactide-co-glycolide), poly(ethylene-vinyl acetate), poly(hydroxybutyrate-covalerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly(ether-esters) such as PEO/PLA, polyalkylene oxalates, polyphosphazenes, and polyarylates including tyrosine-derived polyarylates. According to another exemplary embodiment, the polymeric materials can be natural bioabsorbable polymers such as, but not limited to, fibrin, fibrinogen, cellulose, starch, collagen, and hyaluronic acid. "Biodegradable", "bioerodable", and "bioabsorbable" are used herein interchangeably.

Figure 2A:
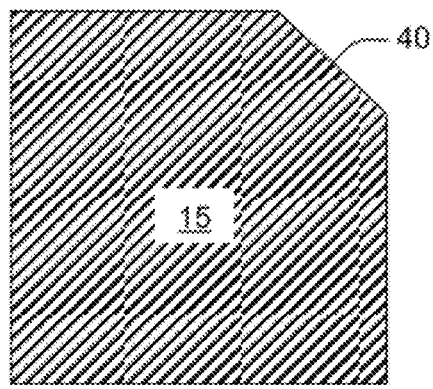
FIGS. 2A-D are diagrammatic representations of side views of representative anti-infective articles.
Figure 2B:
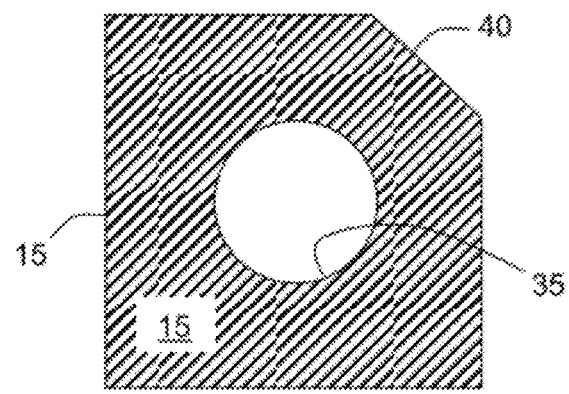
Figure 2C:
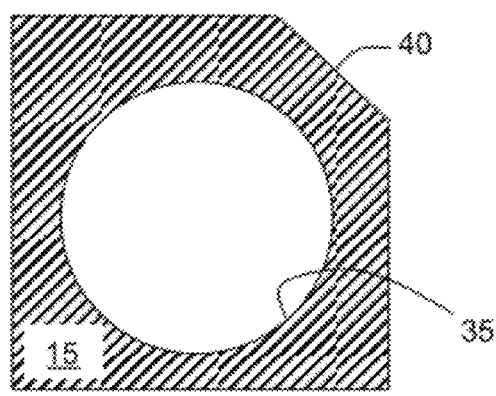
Figure 2D:
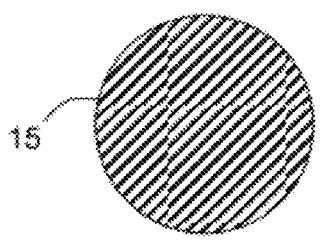

As shown in FIG. 2A-C, article 15 may be in the form of a boot designed to be placed around device 50. Boot 15 may contain an edge opening 40 to allow for connection of an associated device 70. Boot 15 may (FIGS. 2B-C) or may not (FIG. 2A) include one or more side hole 35, which may be of any suitable size. As shown in FIG. 2D, article 15 may be in the form of a disc.

Figure 3:
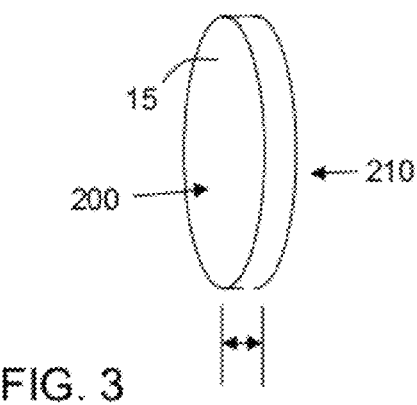
FIG. 3 is a diagrammatic representation of a perspective view of a representative article having a thickness.

As shown in FIG. 3, article 15 has first 200 and second 210 opposing major surfaces, and a thickness. In various embodiments, the article 15 has an average thickness of 0.01 inches (0.026 cm) or less. For example, article 15 may have an average thickness of 0.0075 inches (0.019 cm) or less or 0.005 inches (0.013 cm). In various embodiments, article 15 has an average thickness that allows for 60% or more (e.g., 70% or more, 80% or more, etc.) of anti-infective agent associated with the article to elute within 24 hours of being implanted in a patient. In some embodiments, substantially all of the antimicrobial agent is eluted within 72 hours. In some embodiments, substantially all of the antimicrobial agent is eluted within 24 hours.

Article 15 is placed generally in proximity to device 50 in use. For example, article 15 may be placed in subcutaneous pocket 140 or may be placed on or about device 50. In various embodiments, article 15 is bonded, adhered to, coated on, or otherwise attached to housing 55. Referring to FIG. 4, various locations of article 15 relative to device 50 are shown. The article 15 shown in FIG. 4 is a disc, but it will be understood that the discussion that follows will be applicable regardless of shape or form of article 15. Whether or not bonded, adhered, or coated on device 50, article 15 may be generally centered on a side of housing 55 (FIG. 4A), placed on or over a portion of connector block 60 (FIG. 4B), or otherwise located in proximity to device 50 (FIG. 4C).

As shown in FIG. 4, first major surface 200 of article 15 may be in contact with device 50 and second major surface 210 may be facing away from the external surface of device 50. Surprisingly and as shown in the Example that follows, the surface area of the second major surface 210 of article 15 may be only a small percentage of the external surface area of device 50 to effectively prevent infection. In various embodiments, the surface area of the second major surface 210 is 30% or less, 20% or less, 10% or less, or 5% or less than the external surface area of device 50. As used herein, "surface area" is calculated on a macroscopic scale. For example, a smooth surface will be considered to have the same surface area as a rough or porous surface. One suitable way of calculating the relative surface area of the second major surface 210 of article 15 to the external surface area of device 50 is to determine the percentage of the external surface of device 50 that the second major surface 210 of article 15 covers when in contact with device 50.

An anti-infective agent may be present in an eluting article at any suitable concentration. For example, an anti-infective agent may comprise 0.1% to 50%, 0.1% to 20%, 0.1% to 5%, 1% to 10%, etc. of the weight of the article. In various embodiments, one or more anti-infective agent may be present in the article in an amount of 0.25 to 1% by weight of the article. Anti-infective agent may be incorporated into an article in a variety of ways. For example, anti-infective agent can be covalently grafted to a polymer of the article 15, either alone or with a surface graft polymer. Alternatively, anti-infective agent may be coated onto the surface of the article 15 either alone or intermixed with an overcoating polymer. Anti-infective agent may be physically blended with a polymer of an article 15 as in a solid-solid solution. Anti-infective agent may be impregnated into a polymer of an article 15 by swelling the polymer in a solution of the appropriate solvent. Any means of incorporating anti-infective agent into or on an article 15 may be used, provided that anti-infective agent may be released, leached or diffuse from article 15 on or after contact with bodily fluid or tissue. Regardless of how an anti-infective agent or agents are associated with article 15, it is desirable that agent or agents are incorporated in an amount effective to prevent, reduce the severity, or delay an infection.

For example, it has been surprisingly shown (see Example below) that articles 15 including as low as about 150-200 micrograms of minocycline and 150-200 micrograms of rifampin were able to successfully prevent infection in proximity to a device 50 implanted in a subcutaneous pocket 140. In various embodiments, between about 100-2000 micrograms of rifampin and between about 100-2000 micrograms of minocycline are loaded into, mixed with, or otherwise associated with article 50.

In various embodiments, at least 200 micrograms of minocycline and rifampin are capable of being eluted from article 15 in a 24 hour time period between six and seven days, between five and six days, between four and five days, between three and four days, between two and three days, between one and two days, or within one day following implantation. Alternatively, or in addition, article 15 may contain 300 micrograms or less of minocycline or rifampin seven, six, five, four, three, two, or one day following implantation.

Another way to express effective amounts of anti-infective agents is per external surface area of device 50. For example, in various embodiments, between 1 and 500 micrograms (e.g., between 1 and 100 micrograms, between 3 and 50 micrograms or between 5 and 25 micrograms) of minocycline per square inch of the external surface area of device 50 and between 1 and 500 micrograms (e.g., between 1 and 100 micrograms, between 3 and 50 micrograms or between 5 and 25 micrograms) of rifampin per square inch of the external surface area of device 50 are used to prevent, reduce severity, or delay onset of an infection. In various embodiments, one or more anti-infective agent is associated with article 15 such that an amount of the anti-infective agent is present per external surface area of device 50. One way to determine a suitable amount of the anti-infective agent is to multiply the minimum inhibitory concentration (MIC) of the anti-infective agent against a strain of S. aureus in an amount per milliliter by the product of one milliliter times a number between the range of 1,500 and 50,000; i.e., (MIC) times (1 ml) times (between 1,500 and 50,000).

Articles 15 may comprise polymeric materials designed to control the rate at which an anti-infective agent is released, leached, or diffused from the polymeric material. As used herein, "release", "leach", "diffuse", "elute" and the like are used interchangeably when referring to an anti-infective agent with respect to an article serving as a vehicle for delivering the anti-infective agent. Any known or developed technology may be used to control the release rate. For example, a coating layer may be designed according to the teachings of WO/04026361, entitled "Controllable Drug Releasing Gradient Coating for Medical Devices." Porosity of article may also affect release rate of an anti-infective agent, once implanted. Porous materials known in the art include those disclosed in U.S. Pat. No. 5,609,629 (Fearnot et al.) and U.S. Pat. No. 5,591,227 (Dinh et al.). Typically polymers are non-porous. However, non-porous polymers may be made porous through known or developed techniques, such as extruding with $CO_2$ or by foaming the polymeric material prior to extrusion or coating. By way of another example, the thickness of the article may have effects on the release rate.

As shown in the Example that follows, it has been surprisingly shown that an article 15 that releases a substantial amount of anti-infective agent in a short period of time, as opposed to sustained long duration release, is effective at preventing infection associated with implantation of device 50. In various embodiments, article 15 is configured to elute 60% or more (e.g., 70% or more, 80% or more, etc.) of anti-infective agent associated with the article within 24 hours of being implanted in a patient 10. In some embodiments, substantially all of the antimicrobial agent is eluted within 72 hours. In some embodiments, substantially all of the antimicrobial agent is eluted within 24 hours.

In various embodiments, article 15 is configured to elute 40% or more of anti-infective agent associated with the article within 48 hours of being implanted in a patient 10. In some embodiments, substantially all of the antimicrobial agent is eluted within one week.

EXAMPLE

Silicone boots and discs loaded with minocycline and rifampin were placed about or in contact with an implantable pulse generator and implanted into rabbits along with an inoculum of S. aureus to determine whether such boots or discs would prevent an infection from developing.

I. Methods

A. Boot and Disc Preparation

Silicone boots for disposing about Restore® implantable neurostimulators (Medtronic, Inc.) and having a thickness of 0.015 inches ("thick") or 0.005 inches ("thin") were formed from LSR (Dow Corning 4850) or ETR (Dow Corning 4735) by molding or dip covering. 1.25 inch diameter discs were punched from the boot to create side holes on either side of the boot. The punched discs were sutured to Restore® implantable neurostimulators and were also evaluated for their ability to prevent infection from forming.

B. Drug Loading

Minocycline and rifampin were incorporated into the boots, with or without side holes, and discs as follows. Silicone material was pre-extracted with butyl acetate to remove non-cross-linked polymer. After drying, the pre-extracted silicone was treated in a minocycline/rifampin solution prepared by dissolving 1 gram of minocycline (Mincycline HCl, USP, Chemos, GmbH) in a sodium hydroxide (0.1 gram) in methanol (10 milliliter) solution, then adding 2 grams of rifampin (USP, Spectrum Chemical Mfr. Corp.) and butyl acetate (56.7 milliliter). The solution was sonicated at 40° C. for 45 minutes then allowed to cool to room temperature. At room temperature the silicone was submerged fully and agitated in solution for 1 hour. After one hour the silicone was removed, rinsed twice with methanol, blot dried and allowed to dry overnight. Following drug loading the anti-infective articles were sterilized by ethylene oxide (ETO) (exposure time ~75 min: 130 g of gas used [800-900 mg/L], relative humidity ~65% at 65 kPa/50° C.), except for thick boots (see FIG. 9), which were e-beam sterilized (Acsion: Calibrated at 20° C., using FWT dosimeters that are heat aged—on a single doe measurement the maximum uncertainty is estimated to be +/−6% at a 95% confidence level—Specified dose: 20-31.6 kGy Actual dose: 22.2-31.6 kGy).

C. Extraction and Drug Loading Analysis

Minocycline and rifampin were extracted from the ETO sterilized boots and discs and subjected to HPLC analysis to determine the amount of drug loaded, generally as follows:

1. Extraction from Boot

Each boot was cut into pieces (24) with scissors so that they were small enough to be submerged in the extraction volume (10-20 milliliters of solvent/gram of polymer). The pieces were extracted together in a 60-125 milliliter jar w/top. All the pieces were placed in a jar, and 4:1 THF/ethanol (50 milliliters for thick boots; 15 milliliters for thin boots) was added. The pieces were allowed to swell, and the drug was extracted for 1 hour ($1^{st}$ extraction). The extract was then collected and transferred to a 25-100 milliliters volumetric flask. A second 4:1 THF/ethanol (50 milliliters for thick boots w/holes; 10 milliliters for thin boots with holes) extraction was added to the jar, and the transfer pipette was rinsed with this second extract and discarded. The pieces were allowed to swell, and the drug was extracted for 1 hour ($2^{nd}$ extraction). The extract was then collected and transferred to the 25-100 milliliters volumetric flask containing the first extract. A small amount of extra solvent was needed to make up to volume due to solvent lost to evaporation and polymer swell. This amount also served as a final rinse of both the polymer and the transfer pipette.

2. Extraction from Discs

Desired sized discs (1-1⅝16") were cut from the drug loaded sheet stock with a die press. The discs were sterilized with ETO (as above) and placed in a ounce jar w/top, and 4:1 THF/ethanol (5 mL) was added. The disc was submerged fully in the 4:1 THF/ethanol system. The solution was stirred slowly on an orbital shaker. The disc was allowed to swell, and the drug was extracted from 1 hour ($1^{st}$ extraction). The extract was then collected and transferred to a 10 milliliter volumetric flask. A second 4:1 THF/ethanol (5 milliliters) extraction was added to the jar, and the transfer pipette was rinsed with this second extract and discarded. The resultant solution was slowly stirred on an orbital shaker. The disc was allowed to swell, and the drug was extracted for 1 hour ($2^{nd}$ extraction). The extract was then collected and transferred to the 10 mL volumetric flask containing the first extract. A small amount of extra solvent was needed to make up to 10 mL due to solvent lost to evaporation and polymer swell. This amount also served as a final rinse of both the polymer and the transfer pipette.

3. HPLC Sample Preparation for Extraction Content Analysis

An aliquot of the solution in the volumetric flask was transferred to a HPLC vial (no additional dilution was required). THF/ethanol/drug extracts were added to the 1.5 milliliter HPLC vial. The HPLC vial was place in a refrigerated auto sampler (4° C.) and run, generally as follows.

4. HPLC Method

Chromatographic conditions were as follows. Instrument (Agilent 1100 stack); Column (Prodigy analytical column—150×4.6 mm); Detection mode (UV detection at 238 nm); Flow rate (1.0 mL/min); Column temperature (25° C.); Injection volume (10 uL); Mobile phase A (1.4 g/L dibasic sodium phosphate buffer pH 6.8); Mobile phase B (ACN 100%); and Gradient:

| Time (min). | % B |
|---|---|
| 0 | 12 |
| 10 | 36 |
| 25 | 75 |

The run time was 25 minutes, and the post time was 5 minutes.

Minocycline, rifampin and all known impurities have good solubility in methanol and THF/ethanol 4:1.

D. Drug Elution

ETO sterilized drug loaded discs (thick and thin) were implanted subcutaneously in the back of New Zealand white rabbits (albino rabbits, *Oryctolagus cuniculus*, white strain). The discs were removed from the rabbits at 1, 3, 7 and 14 days. The drug contents of the explanted discs were compared to the contents of the discs at the start of the experiment. An elution profile was generated based on the difference.

In addition, in-vitro drug elution studies were performed on 0.005", 0.010" and 0.015" thick drug loaded Dow Corning Silicone 4850 discs. A monobasic sodium phosphate buffer (1.2 g/mL) solution at pH-6 was used as the elution media. The silicone test articles are submerged in the solution (20-40 mL solution/gram polymer) in small jars (typically 1 oz.) with nylon mesh screens to keep the test articles from floating to the surface. The jars are placed in an oscillating water bath at 37° C. to mimic physiological conditions. The media is replaced and assayed by HPLC periodically, to determine drug content eluted.

E. Additional In-Vivo Studies

Rifampin and minocycline loaded boots and discs were sterilized by ethylene oxide (exposure time ~75 min: 130 g of gas used [800-900 mg/L], relative humidity ~65% at 65 kPa/50° C.). The sterilized boots were placed about Restore® implantable neurostimulators and the sterilized discs were sutured to the connector block of the neurostimulators. The neurostimulators and associated anti-infective article (neurostimulators alone served as control) were implanted in a pocket formed in the back of New Zealand white rabbits (albino rabbits, *Oryctolagus cuniculus*, white strain) with or without lead extensions (Two lead extensions, model 37082, Medtronic, Inc.). An inoculum of *Staphylococcus aureus* (original primary source was ATCC 29213-tested culture obtained from an infected pocket in a previous study) was introduced into the subcutaneous pocket.

Briefly, a 2.0-2.5 cm lateral incision along the ventral surface of the spine was created through the dermal layer. A single incision was made parallel to the mid-line of the back, cutting through the fascia and exposing the para vertebral muscle. The fascia membrane and portion of the trapezius muscle was incised with a scalpel creating a nominal implant site. Bleeding was controlled with gauze and pressure. Using blunt dissection, an implant pocket was created along the left lateral wall toward the lateral aspect of the left scapula of the rabbit. The pocket extended approximately 3-4 cm toward the hamate process. Once the pocket was created, a sterile INS device with or without cover was inserted into the pocket. A bacterial injection cannula was created by removing the distal needle from a Vacutainer® blood collection set (Becton, Dickinson and Company). The 1.5 mm tube was placed into the pocket between the INS device and the infraspinous fossa of the scapula. The tube was temporarily secured with a purse-string suture. The deeper facial layer of the mid-line skin incision was closed with absorbable sutures. The pocket was closed using a mattress stitch and 3.0 prolene sutures reconnecting the subcutaneous tissues. The cutaneous tissues was then closed using 3.0 prolene sutures and interrupted stitches leaving only the distal end of the cannula in the pocket. A syringe was used to inject $5 \times 10^3$ colony forming units (CFU) of *S. aureus* into the pocket using the cannula followed by 1.0 mL of sterile saline from a separate sterile syringe. The cannula was removed and the purse-string suture was closed to seal the pocket. Animals were observed daily over the course of 7 days. Surgical wounds associated with the implant were sutured. The neurostimulators were explanted seven days following implantation. The rabbits and neurostimulators were then checked for the presence of an infection. Animals will be observed daily over the course of 7 days looking for signs of illness, injury, or abnormal behavior. At termination blood was drawn for bacterial culture. The INS/extension and depleted cover were removed from the pocket. The cover was removed from the INS. The extensions were removed from the INS. The cover, INS, and extensions were agitated separately to remove adhered and nonadhered bacteria, this liquid was then cultured. The pocket was swabbed and cultured. If any of these five bacteria checks (blood, pocket, cover, INS, extensions) were positive then this was determined to be a positive animal.

Seven rabbits received an INS in a thin boot with side holes and no extension, five received an INS in a thin boot with side holes and extension, seven received an INS in a thick boot with side hole and no extensions, twenty (ten each, in two different studies) received an INS in a thick boot and no extensions, seven received an INS with a thin disc with no extensions, five received an INS with a thin disc with extensions, and seven received an INS with a thick disc with no extensions. In all, 32 control animals received an INS alone (four studies using 5, 7, 10, and 10 control animals).

Drug loading and elution (7 day) analysis were performed as described above.

II. Results and discussion

A. Drug Elution

Figure 5:
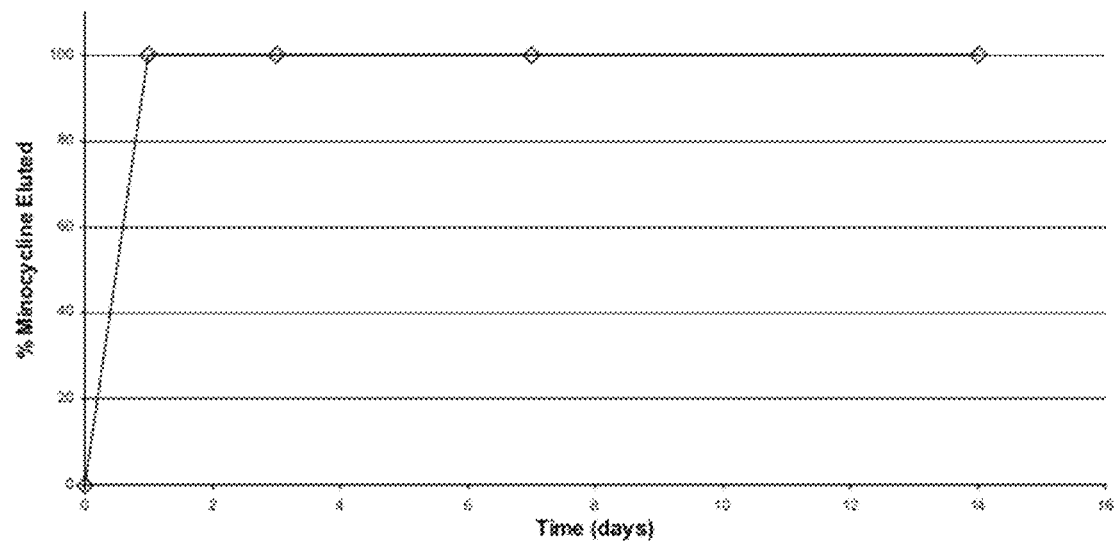
FIG. 5 is a graph showing the elution profile of minocycline out of thin silicone anti-infective articles.
Figure 6:
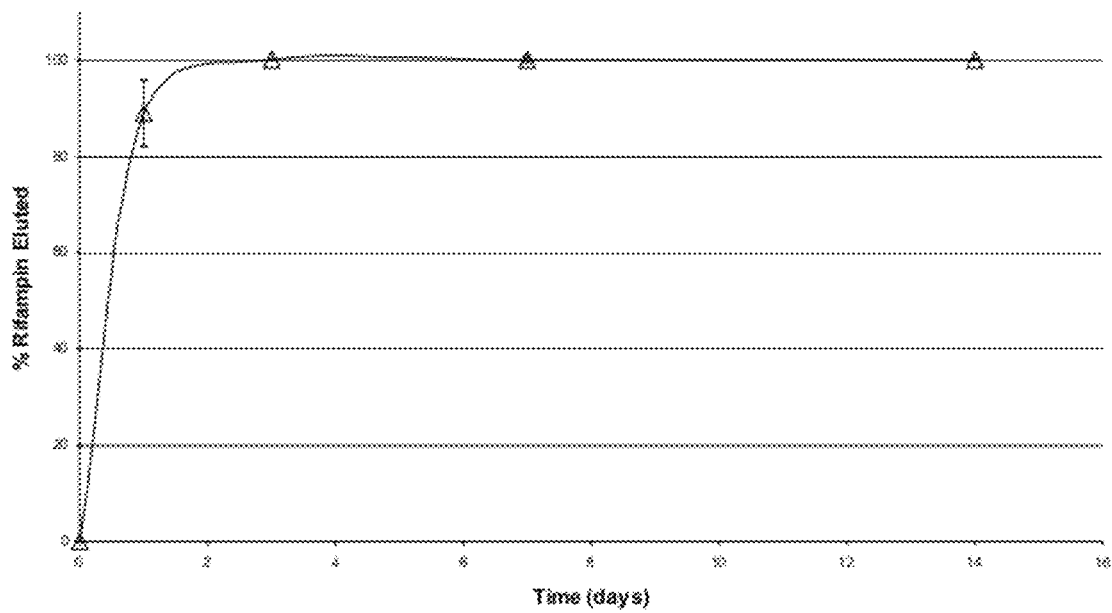
FIG. 6 is a graph showing the elution profile of rifampin out of thin silicone anti-infective articles.

The rates of elution (shown as percentages) of minocycline and rifampin from thin discs implanted in rabbits are shown in FIGS. 5 and 6, respectively. It is expected that thin boots should have similar elution profiles, assuming sink conditions when implanted. As can be seen, substantially all the minocycline and about 85% of the rifampin were eluted within 24 hours. Within three days, essentially all the rifampin was eluted. Surprisingly, discs with such rapid elution profiles were able to effectively prevent infection formation (see FIG. 9).

Figure 7:
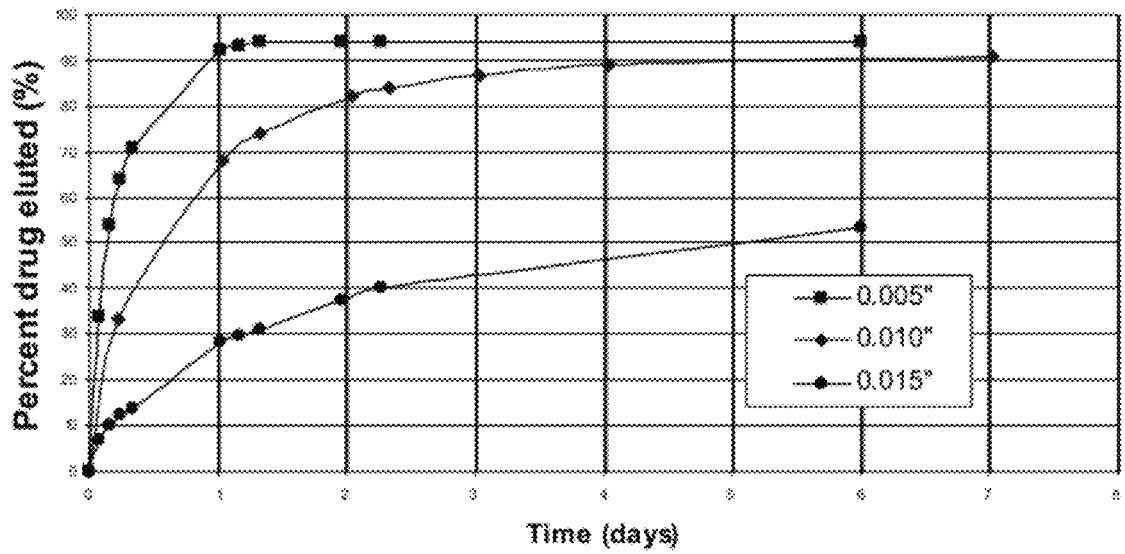
FIG. 7 is a showing the elution profile of minocycline out of thin silicone anti-infective articles.
Figure 8:
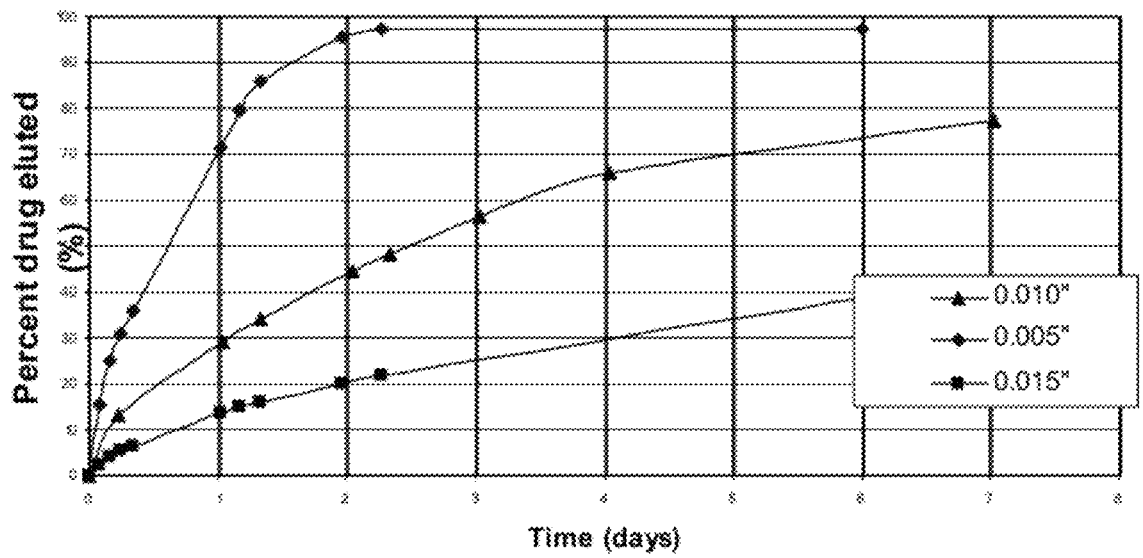
FIG. 8 is a graph showing the elution profile of rifampin out of thin silicone anti-infective articles.

The in vitro rates of elution (shown as percentages) of minocycline and rifampin from thin discs are shown in FIGS. 7 and 8. The elution profiles of 0.005" thick discs were similar in vivo to in vitro. However, it is worth noting that the in vitro studies allow for a determination of how much drug was actually eluted, while the in vivo studies allow for a determination of how much drug remained. As such, the results in vitro do not show 100% elution presumably because some of the drug degrades during test conditions, and thus released drug is not detected. Regardless, as can be seen from FIGS. 7 and 8, substantially all the minocycline was eluted from the thin discs within a day, and substantially all the minocycline was eluted from the thin discs with two days.

As can be seen in FIGS. 7 and 8, it took considerably longer for a high percentage of the drugs to elute from the 0.01" and 0.015" thickness discs than from the thin discs. It should be noted that the percentage of drug eluted from the thick discs was considerably lower (less than 60%) than that of thin discs (greater than 90%). It is believed that this is due to increased degradation of drug in the thick discs as time passes. That is, because it takes longer for drug to elute from the thick discs, there is more time for the drug to degrade before it elutes. Accordingly, it is believed that more degradants are eluted from thicker discs. Exposing patients to increased levels of degradants may prove undesirable.

The elution profile of the 0.01" discs may serve to provide an elution profile that could be clinically very efficacious. As shown in FIGS. 7 and 8, greater than 90% of minocycline eluted from the discs in a week, with about 70% eluting in a day, and nearly 80% of the rifampin eluted in a week, with more than 40% eluting in two-days. It has also been found that e-beam sterilized 0.01" thickness boots with two side holes can elute at least 200 micrograms of rifampin between 4.5 and 5.5 days (3 to 4 days for ETO sterilized boots) after elution testing begins (not shown). Further ETO sterilized 0.01" boots with two side holes can elute greater than 167 micrograms of minocycline and greater than 200 micrograms of rifampin in the time period between two and three days (not shown).

As discussed in more detail below and as shown in FIG. 9, thin discs containing as little as 168 micrograms of minocycline and 193 micrograms of rifampin were effective at preventing infection. Accordingly, the ability of 0.01" thick silicone material to elute minocycline or rifampin at such levels at two to three or 4.5 to 5.5 days, may prove to provide a very effective clinical outcome with little adverse effects.

B. Additional In-Vivo Studies

The amounts of minocycline and rifampin loaded can be seen the table presented in FIG. 9. As can be seen, amounts of minocycline as low as 168 micrograms and rifampin as low as 193 micrograms were effective at preventing infection (Thin Disc). In seven out of seven rabbits implanted without extensions and five out of five rabbits implanted with extensions, infection was prevented by discs loaded with between 168-190 micrograms of minocycline and 193-203 micrograms of rifampin. It was also surprising that minocycline in the range of 778-869 micrograms and rifampin in the range of 832-998 micrograms (Thin Boot—2 Holes) was effective in prevent infection in seven out of seven rabbits implanted without extensions and five out of five rabbits implanted with extensions. In each of the above-studies, all control animals (INS only, no disc or boot) had developed an infection in the surgical pocket (twelve out of twelve). It should be noted that the virulence of the infection appears more severe in control rabbits receiving the extensions in addition to the INS. Thus, the efficacy of such low doses of anti-infective agent in animals implanted with both INS and extensions is notable.

As discussed above with regard to the drug elution studies, it was also surprising that boots and discs that elute a substantial portion of their anti-infective agent within one day and that elute essentially all of their anti-infective agent within three days were effective at preventing infection in the rabbits.

The surface area of the discs (1.23 square inches) was about 11% that of the surface area of the neurostimulator (13 square inches), yet even with the thin discs having relatively low drug loaded no infection was observed with the use of such discs (see, FIG. 9—Thin Disc).

While not tested, a thin (0.005 inches) boot having no side holes would be expected to be able to be loaded with about three times the amount of minocycline or rifampin as the thin boot with two holes, because the thick boot with no holes was loaded with about three times the amount of minocycline and rifampin as the thick boot with two side holes.

C. Additional Discussion

While ETO sterilization was used in many of the studies described herein, e-beam sterilization may result in anti-infective articles from which more minocycline and rifampin may elute (relative to ETO sterilization). See, e.g., U.S. patent application Ser. No. 11/535,762, entitled "STERILIZED MINOCYCLINE AND RIFAMPIN-CONTAINING MEDICAL DEVICE", filed Sep. 27, 2006, which patent application is hereby incorporated herein by reference in its entirety to the extent that it does not conflict with the disclosure presented herein.

The minimum inhibitory concentration (MIC) of rifampin against the strain of S. aureus used in the studies discussed above was determined to be 0.06 micrograms/milliliter. Accordingly, one of skill in the art can readily apply the teachings herein to other anti-infective agents to determine an effective amount of the anti-infective agent, once the MIC of the anti-infective agent is determined. For example, if the MIC of the anti-infective agent is similar to that of rifampin, then similar amounts of the anti-infective agent may be used. If the MIC of the anti-infective agent is ten times higher than the MIC for rifampin, ten times more of the anti-infective agent may result in an effective amount of the anti-infective agent.

Thus, embodiments of the REDUCTION OF INFECTION ASSOCIATED WITH MEDICAL DEVICE are disclosed. One skilled in the art will appreciate that the present invention can be practiced with embodiments other than those disclosed. The disclosed embodiments are presented for purposes of illustration and not limitation.

What is claimed is:

1. An implantable medical system comprising:
   an implantable medical device having an exterior surface area; and
   an article configured to contact the exterior surface of the device, wherein the article includes an effective amount of minocycline and rifampin, and wherein the article is configured to elute 80% or more of the minocycline and rifampin within three days of being implanted in a patient;
   wherein minocycline is present in the article in an amount between 3 and 50 micrograms per square inch of the exterior surface area of the device and wherein rifampin is present in the article in an amount between 3 and 50 micrograms per square inch of the exterior surface area of the device.

2. The system of claim 1, wherein the article is configured to elute substantially all of the minocycline and rifampin within a week of being implanted in a patient.

3. The system of claim 1, wherein the article is biodegradable.

4. The system of claim 1, wherein the article has an average thickness of 0.01 inches or less.

5. The system of claim 1, wherein the article has an average thickness of 0.0075 inches or less.

6. The system of claim 1, wherein the article has an average thickness of 0.005 inches or less.

7. The system of claim 1, wherein the article is configured to elute 40% or more of the minocycline and rifampin within 48 hours of being implanted in a patient.

8. The system of claim 1, wherein the article configured to elute 60% or more of the minocycline and rifampin within 24 hours of being implanted in a patient.

9. The system of claim 1, wherein the article has first and second opposing major surfaces, with the first major surface is configured to be adhered to the surface of the device and the second major surface of the article has a surface area of 30% or less than the exterior surface area of the device.

10. The system of claim 1, wherein minocycline is present in the article in an amount between 5 and 25 micrograms per square inch of the exterior surface area of the device and wherein rifampin is present in the article in an amount between 5 and 25 micrograms per square inch of the exterior surface area of the device.

11. The system of claim 1, wherein the article is a polymeric disc.

12. An implantable medical system comprising:
    an implantable medical device having an exterior surface area; and
    an article configured to contact the device and including (i) minocycline in an amount of between 3 and 50 micrograms per square inch of the exterior surface area of the device and (ii) rifampin in an amount between 3 and 50 micrograms per square inch of the exterior surface area of the device.

13. The system of claim 12, wherein minocycline is present in the article in an amount between 5 and 25 micrograms per square inch of the exterior surface area of the device and wherein rifampin is present in the article in an amount between 5 and 25 micrograms per square inch of the exterior surface area of the device.

14. An implantable medical system comprising:
    an implantable medical device having an exterior surface area; and
    an article having first and second opposing major surfaces, the first major surface configured to contact the exterior surface of the device and the second major surface having a surface area of 30% or less than the exterior surface area of the device and being configured to contact tissue of a patient when implanted,
    wherein the article includes an effective amount of minocycline and rifampin;
    wherein minocycline is present in the article in an amount between 3 and 50 micrograms per square inch of the exterior surface area of the device and wherein rifampin is present in the article in an amount between 3 and 50 micrograms per square inch of the exterior surface area of the device.

15. The system of claim 14, wherein minocycline is present in the article in an amount between 5 and 25 micrograms per square inch of the exterior surface area of the device and wherein rifampin is present in the article in an amount between 5 and 25 micrograms per square inch of the exterior surface area of the device.

* * * * *